(12) United States Patent
Williams

(10) Patent No.: US 6,193,374 B1
(45) Date of Patent: Feb. 27, 2001

(54) OPHTHALMIC APPARATUS

(76) Inventor: Grady J Williams, 5724 Desert Skyway, Las Vegas, NV (US) 89149

( * ) Notice: Subject to any disclaimer, the term of this patent is extended or adjusted under 35 U.S.C. 154(b) by 0 days.

(21) Appl. No.: 09/476,518

(22) Filed: Jan. 3, 2000

(51) Int. Cl.[7] ..................................... A61B 3/00
(52) U.S. Cl. ............................................ 351/245
(58) Field of Search .......................... 351/200, 205, 351/245, 246, 206, 221; 248/157, 419, 420, 424

(56) References Cited

U.S. PATENT DOCUMENTS 4,643,547   2/1987   Collins et al. .
5,717,480 * 2/1998   Brooks et al. ..................... 351/221

* cited by examiner

Primary Examiner—George Manuel
(74) Attorney, Agent, or Firm—John D. Jeter

(57) ABSTRACT

An ophthalmic instrument support apparatus has a generally cylindrical base with top and bottom ends and an instrument support post that is, preferably, telescopably received in the base to extend upward an adjustable distance. A laterally extending arm is detachably secured to said post and arranged to receive an ophthalmic instrument on the extended end. The base is arranged to rest on a floor. The base has legs that are extendible from base to engage the floor for stability. An optional over-the-lap table is provided, with means to attach one end to the base, with a leg to support the distal end. The base is arranged with doors to receive a selected set of ophthalmic instruments, in the base and on the doors, for storage and protection during transport.

6 Claims, 1 Drawing Sheet

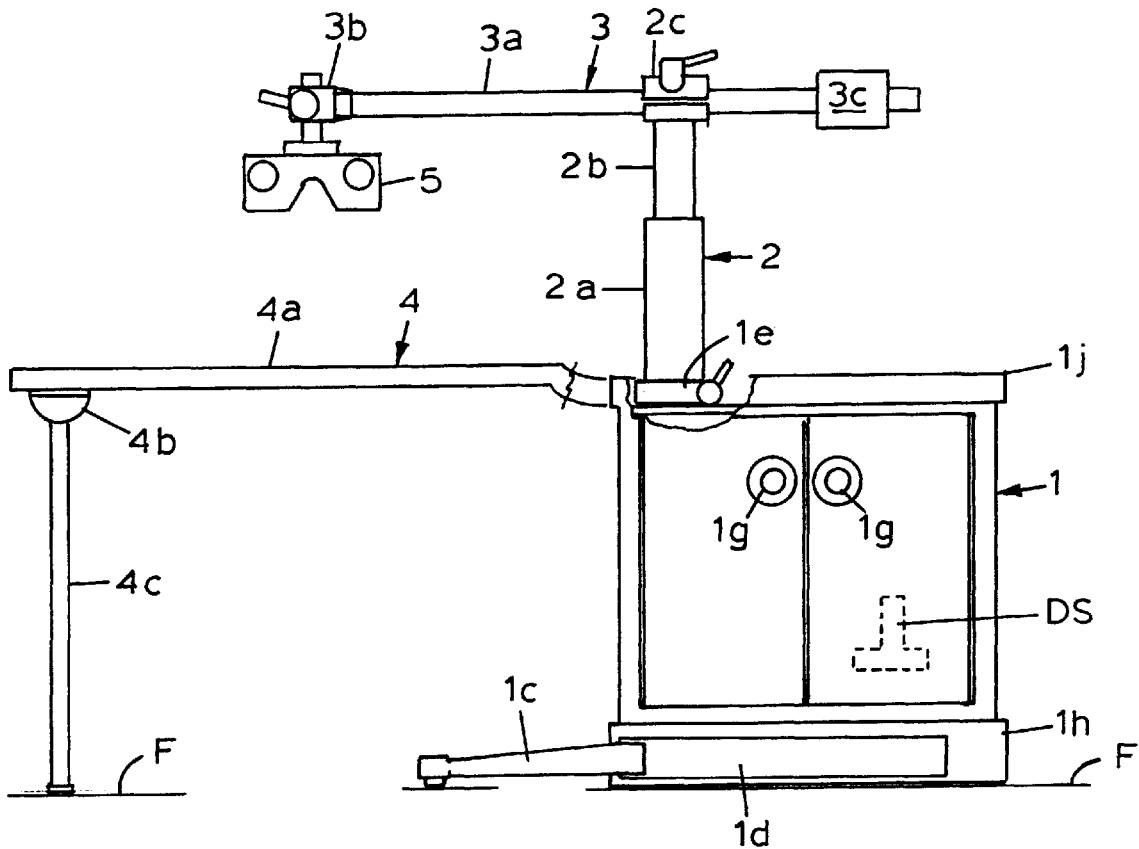
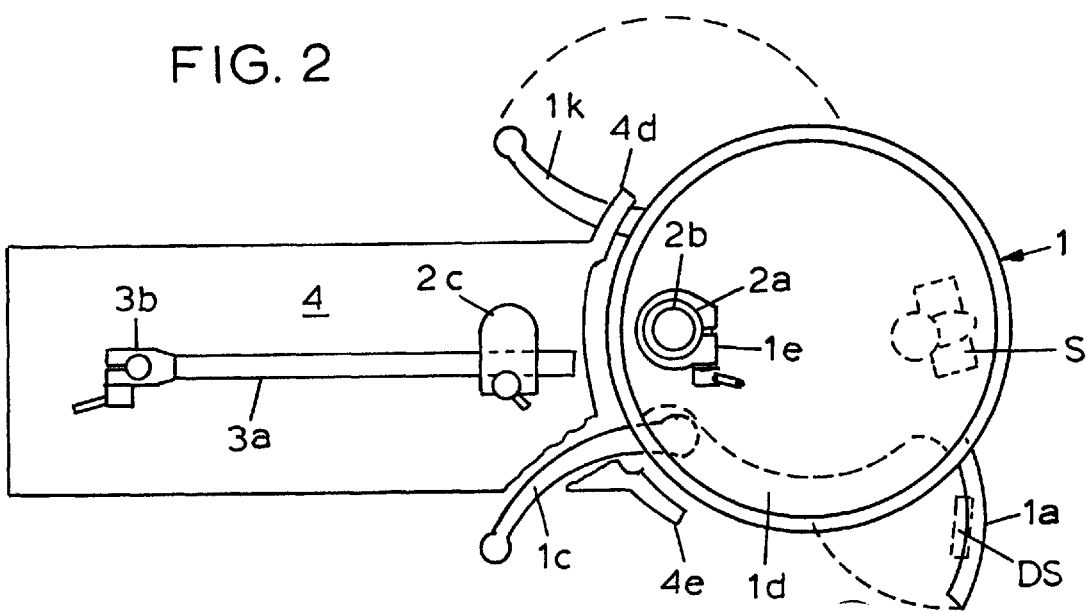

OPHTHALMIC APPARATUS

This invention pertains to equipment used primarily in ophthalmic clinics to test the vision characteristics of patients for the purpose of fitting visual aids. Emphasis is upon portability and compactness of equipment and equipment storage and utilization.

BACKGROUND

Operatories used for visual testing of patients for the purpose of correcting visual problems normally utilize rather expensive and heavy equipment. The usual operatory equipment includes elevator chairs for patients. The optical equipment and the supporting and positioning arrangements have been heavy. Such apparatus is usually in fixed positions in dedicated operatories. The obligation of patients to go to established offices for check-ups has not been considered a major problem. On a global basis, that ability is not universal. The industry has not responded to the need to move ophthalmic related equipment to remote areas and to provide the needed equipment to areas not situated to justify full featured operatories within useful travel range of all those in such need.

The patient distribution and the ability of modern designs justify a novel approach to patient services. Modern optical equipment is lighter due to modern materials and designs and can be supported and managed by less massive ancillary equipment. Movement of the patient to an operatory may involve one or more third parties for transport and assistance. The population distribution now places many patients in situations such as nursing homes and other institutions. In the institutional setting several patients may be available for needed attention by ophthalmologists and optometrists. The burden of mobility has shifted to favor moving the operatory to the patient. To that end new features are needed in equipment design and construction. The need for elevator chairs can be offset by novel optical equipment concepts. There is a need for a table to extend above the lap of the patient to receive various table supportable optical instruments. Recent innovations have led to extending the table from the ophthalmic instrument stand without distal end support. That arrangement has added weight requirement to the supporting base. If the table has distal end support by a floor standing leg, some of the base weight requirement is relieved, but that has not been the thrust of development. Several optical contrivances are found in operatories and their collective transport can be a damage hazard. The mobility approach needs to address the whole of the device setup.

SUMMARY OF INVENTION

An ophthalmic testing package is provided that supports the needed instruments in position for the comfort of patients seated in standard chairs, and encloses the various optical accessories that pertain to that function. The apparatus, by folding and enclosing, condenses to a package of such size and weight that it can be handled by one individual. The package, once condensed, is in a ruggedized state and can survive a reasonable amount of common travel and transport abuse. The one main package, a generally cylindrical base, has a post telescopingly received within the base that comprises the optics stand, or post. The apparatus that extends to the seated patient is reduced in weight to minimize the risk of tilting the base. The base, optionally, has folding extension legs to further stabilize the base. As an alternative, a table is provided that is removably fastened to the base at one end and is supported at the distal end by a foldable, floor standing, leg. The fastening means between table and base reduces the tilting prospect and reduces the need for folding stabilizer legs extendible from the base.

The ophthalmic instrument support post is preferably tubular and biased to rise from the base when a positioning friction clamp is released. The bias force, either gas pressure or a spring, is arranged to support the post with the usual instrument load attached.

The instrument is supported on an extendible arm that is releasably secured to the post. The post preferably telescopes into the base and is biased upward and has clamping means to secure the post at selected heights from the base. The extending bias is provided by springs or gas cylinder means, Gas pressure extension is preferred. Instrument height can be adjusted by vertical movement of the post. The arm is, preferably, of tubular construction with arrangement to slide it through a clamp on the post. Other arm arrangements, with a preferred means for extension, can be used.

The base is a storage unit for various instruments, with doors that swing open for access. Inside the doors, fittings are provided for the ophthalmic instrument, and other instruments normally used atop tables or on the arm.

The apparatus is usable to extend the capacity of a fixed operatory facility and will accommodate ophthalmic instruments available there by changing the means to attach adjustable extension arms to the post. That adaptation is well within the capabilities of those practicing such art.

It is an object of this invention to provide a transportable container that houses and protects needed optical instruments and serves as a pedestal base for supporting optical equipment when they are extended laterally from the base.

It is another object to provide arrangements within the container to receive and protect various optical units needed in an operatory.

It is yet another object to provide folding stabilizer legs on the base to prevent tilting when in use for examination.

It is still another object to provide a vertical instrument post for instrument support that is telescopingly received within the base for transport.

It is still another object to provide an above-the-lap table, secured to the base, with a distal end support leg to add stability to the base.

These and other objects, advantages, and features of this invention will be apparent to those skilled in the art from a consideration of this specification, including the attached claims and appended drawings.

BRIEF DESCRIPTION OF DRAWINGS

In the drawings wherein like features have similar captions,

FIG. 1 is a side view, partially cut away of the preferred embodiment of the invention.

FIG. 2 is a top view of the apparatus of FIG. 1.

DETAILED DESCRIPTION OF DRAWINGS

In the drawings, features that are well established in the art and do not bear upon points of novelty are omitted in the interest of descriptive clarity. Such omitted features may include threaded junctures, weld lines, sealing elements, pins and brazed junctures, movement brake details and the like.

In FIG. 1 the basic apparatus is shown with the optional table 4 attached to the base 1, with the post 2 extended and supporting extending arm 3. Ophthalmic instrument 5 is attached to the arm by clamp 3b on arm 3a. The arm is movable through clamp 2c to adjust the distance of the instrument from the base. Optional counterbalance mass 3c makes arm 3a slide more easily through clamp 2c.

Base 1 is a generally cylindrical structure having bash rings 1h and 1j at the bottom and top respectively. Doors 1a and 1b close together with piano hinges on the distal sides. Recessed knobs 1g aid in opening the doors. Foldable legs 1c and 1k fold into recesses in the base, one shown as 1d.

Clamp 1e is attached to the top plate of the base and secures post tube 2a in a selected vertical position. Post tube 2b telescopes from tube 2a to achieve the selected height for the clamp 2c, which may rest atop the tube 2b. If the post is to telescope into the base, a guide tube is installed below clamp 1e (not shown). If the post is to be collapsed and stored within the base for transport, clamp 1e secures the post to the base when it is in use. The post is preferably biased for extension and air pressure in the post is preferred. A spring can be used instead.

Legs 1c and 1k are adequate for base stability but may be left stowed in recesses (1d shown) if the table 4 is used. Table 4 has attachment arms 4e and 4d for attachment to the ring 1j by screws (not shown) and, with leg 4c unfolded from bracket 4b to engage the floor F, the base is provided stability. Table top 4a is generally leveled by the leg and the base attachments. The lower end of leg 4c can be provided with a leveling screw. Similar screws can be installed on the ends of legs 1c and 1k.

In FIG. 2, arm assembly 3 is detached from the post 2 and moved to the left to allow a view of the post and clamp arrangement. One door is shown open. Except the table, all shown is to be stored within the base for transport. Arm 3a, being tubular lends itself to threaded connection about the mid length (not shown) to reduce the length for storage in the base.

Several ophthalmic instruments are needed in an operatory. Some are used on table tops and all need protection for transport. Inside the base and on the inside of the doors various recesses and brackets can be fastened to receive and protect the instruments. Those features are adapted to the particular instruments to be protected and are shown symbolically as S within the base and as DS within the doors (one shown). When the apparatus is ready for use, some of the table supported instruments are removed from the base and temporarily placed on the base top, on areas not dominated by the post, for convenient transfer to the table for use.

From the foregoing, it will be seen that this invention is one well adapted to attain all of the ends and objects hereinabove set forth, together with other advantages which are obvious and which are inherent to the apparatus.

It will be understood that certain features and sub-combinations are of utility and may be employed without reference to other features and sub-combinations. This is contemplated by and is within the scope of the claims.

As many possible embodiments may be made of the apparatus of this invention without departing from the scope thereof, it is to be understood that all matter herein set forth or shown in the accompanying drawings is to be interpreted as illustrative and not in a limiting sense.

The invention having been described, I claim:

1. An optical testing apparatus for use by ophthalmologists and optometrists for testing the vision characteristics of patients, the apparatus comprising:

a) a generally cylindrical base for stable placement on a flat surface with the axis vertical, said base provided with at least two legs, said legs arranged to move into said base for storage and to extend from said base to contact said surface to stabilize said base;

b) a pole situated on said base and arranged to be telescopingly received within said base and to extend from said base as required, with locking means to secure the post height in at least one selected position;

c) a laterally adjustable arm removably secured to said pole and arranged to extend laterally therefrom, with means to secure it with the extended end at selected distances from said post.

2. The apparatus of claim 1 wherein said arm has clutch means arranged for single hand release of said arm from said post.

3. The apparatus of claim 1 wherein an over-the-lap table with two ends is provided, detachably secured to said base at one end, with at least one leg extending from the distal end to said surface.

4. An optical testing apparatus for use by ophthalmologists and optometrists for testing the vision characteristics of patients, the apparatus comprising:

a) a generally cylindrical base for stable placement on a flat surface with the axis vertical, said base provided with at least two legs, said legs arranged to move into said base for storage and to extend from said base to contact said surface to stabilize said base;

b) a pole removably situated on said base and arranged with locking means to secure said post to said base;

c) a laterally adjustable arm, with two ends, removably secured to said pole and arranged to extend laterally therefrom, with means to secure it with the extended end at selected distances from said post.

5. The apparatus of claim 4 wherein said arm has clutch means arranged for single hand release of said arm from said post.

6. The apparatus of claim 4 wherein an over-the-lap table with two ends is provided, detachably secured to said base at one end, with at least one leg extending from the distal end to said surface.

* * * * *